United States Patent [19]

Udovich et al.

[11] 4,283,288

[45] Aug. 11, 1981

[54] OXIDATION OF BUTANE TO MALEIC ANHYDRIDE

[75] Inventors: Carl A. Udovich, Joliet; Bernard L. Meyers, Wheaton, both of Ill.

[73] Assignee: Standard Oil Company (Indiana), Chicago, Ill.

[21] Appl. No.: 149,842

[22] Filed: May 14, 1980

[51] Int. Cl.³ .............................................. B01J 27/14
[52] U.S. Cl. .................................... 252/437; 252/435
[58] Field of Search .................................. 252/435, 437

[56] References Cited

U.S. PATENT DOCUMENTS

| | | | |
|---|---|---|---|
| 3,293,268 | 12/1966 | Bergman et al. | 260/346.75 |
| 3,385,796 | 5/1968 | Kerr | 252/435 X |
| 3,832,359 | 8/1974 | Freerhs et al. | 260/346.75 |
| 3,838,067 | 9/1974 | Barker | 260/346.75 |
| 3,864,280 | 2/1975 | Schneider | 252/435 |
| 3,867,411 | 2/1975 | Roffelson et al. | 252/437 X |
| 3,888,886 | 6/1975 | Young et al. | 252/435 X |
| 3,985,775 | 10/1976 | Harrison | 252/437 X |
| 4,002,650 | 1/1977 | Bremer et al. | 260/346.8 A |
| 4,016,105 | 4/1977 | Kerr | 252/437 |
| 4,018,709 | 4/1977 | Barone et al. | 252/435 |
| 4,062,873 | 12/1977 | Harrison | 252/437 X |
| 4,064,070 | 12/1977 | Harrison | 252/437 X |
| 4,080,312 | 3/1978 | Farha Jr. et al. | 252/435 X |
| 4,085,122 | 4/1978 | Stefani et al. | 260/346.75 |
| 4,094,888 | 6/1978 | Straus | 260/346.75 |
| 4,147,661 | 4/1979 | Higgins et al. | 252/437 |
| 4,149,992 | 4/1979 | Mount et al. | 252/435 |
| 4,151,116 | 4/1979 | McDermott | 252/435 |
| 4,152,338 | 5/1979 | Kerr | 260/346.75 |
| 4,152,339 | 5/1979 | Kerr et al. | 260/346.75 |
| 4,158,671 | 6/1979 | Barone | 252/437 X |
| 4,179,404 | 12/1979 | Barone | 252/437 X |
| 4,220,595 | 9/1980 | Dickason et al. | 252/437 X |

FOREIGN PATENT DOCUMENTS

| | | | |
|---|---|---|---|
| 7507583 | 1/1974 | Netherlands | 252/435 |
| 1141343 | 3/1966 | United Kingdom | 252/435 |

*Primary Examiner*—Delbert E. Gantz
*Assistant Examiner*—William G. Wright
*Attorney, Agent, or Firm*—G. J. Blumberg; William T. McClain; William H. Magidson

[57] ABSTRACT

A novel catalyst for the oxidation of butane to produce maleic anhydride comprising a phosphorus and vanadium mixed oxide wherein the catalyst is prepared by using an organic medium and has a specific phase identified by characteristic X-ray pattern. A process for the manufacture of maleic anhydride from butane feedstock utilizing the novel catalyst.

7 Claims, No Drawings

OXIDATION OF BUTANE TO MALEIC ANHYDRIDE

BACKGROUND OF THE INVENTION

1. Field of the Invention

The field of this invention relates to the production of maleic anhydride from n-butane and catalysts therefor.

2. Background

Maleic anhydride is of significant commercial interest throughout the world and is extensively used in the manufacture of alkyd resins. It is also a versatile intermediate for chemical synthesis. Consequently, large quantities of maleic anhydride are produced each year to satisfy these needs. The production of maleic anhydride by the catalytic oxidation of benzene and butene is well known and the principal method currently employed for the manufacture of maleic anhydride is by the air oxidation of benzene in the presence of certain heavy metal oxide catalysts. However, because of the inherent toxicity of benzene fumes, the trend has been to eliminate the utilization of benzene as a feedstock and newer facilities tend to utilize butane oxidation processes.

In general, catalysts proposed for the oxidation of butane to maleic anhydride have been based upon vanadium and phosphorus. In U.S. Pat. No. 3,293,268 it is disclosed that the oxidation of butane to maleic anhydride can be performed in the presence of a phosphorus-vanadium-oxygen containing complex catalyst. Though this catalyst is capable of oxidizing butane, it does not give sufficiently high yields. Yields of maleic anhydride of only 30 to 50 weight percent are reported. Various activators, stabilizers and promoters have been disclosed in the prior art to improve the yields of maleic anhydride. References include U.S. Pat. Nos. 3,864,280, 3,867,411, 3,832,359, 3,888,886, 4,002,650, 4,054,943, 4,147,661, 4,085,122, 4,094,888, 4,149,992, 4,151,116, 4,152,338, 4,152,339 and British Application No. 2,019,839.A. While the aforementioned prior art tends to bring about some improvement in the performance of the phosphorus-vanadium catalyst there remains much room for improvement, particularly from the standpoint of operating temperatures, high conversion and yield.

The object of the present invention is to provide a phosphorus-vanadium oxide catalyst prepared in an organic medium which is in a phase comprising a characteristic powder X-ray diffraction pattern using copper K alpha radiation as follows:

| angstrom | Line Position 2.θ degrees | Intensity |
| --- | --- | --- |
| 5.7 | 15.6 | 67 |
| 4.5 | 19.7 | 47 |
| 3.7 | 24.3 | 36 |
| 3.3 | 27.1 | 53 |
| 3.1 | 28.8 | 26 |
| 2.9 | 30.5 | 100 |
| 2.8 | 32.2 | 17 |
| 2.7 | 33.7 | 20 |

A further object is to provide a process for the manufacture of maleic anhydride from butane at a temperature of about 600° to 750° F. in the presence of the novel catalyst.

The novel catalyst comprises a phosphorus-vanadium mixed oxide. The atomic ratio of the vanadium to phosphorus can suitably be in the range of 0.5:1.0 to 1.25:1.0, preferably in the range of 0.6:1.0 to 1.0:0.9.

Catalysts prepared according to the invention may be made from an organic solvent system wherein vanadium pentoxide is reduced with gaseous hydrogen chloride. Subsequent reaction of the vanadium oxide solution with crystalline orthophosphoric acid and removal of water of reaction by azeotropic distillation results in precipitation of vanadium-phosphorus oxide catalyst which may suitably be filtered from the mother liquor, dried and then employed as an oxidation catalyst for the manufacture of maleic anhydride from butane feedstock. Suitably, organic solvents are alcohols or mixtures of alcohols with aromatic hydrocarbons such as benzene or orthoxylene. Aliphatic alcohols are usually employed in the process and isobutanol is the preferred alcohol. The precipitation of the phosphorus-vanadium oxide complex is achieved by reducing the solubility of this complex in solution by employing a co-solvent. Precipitation can also be effected by reducing the temperature and removal of the solvent. The use of a co-solvent such as benzene or orthoxylene also functions to facilitate removal of excess water through azeotropic distillation. Precipitation of the phosphorus-vanadium oxide catalyst can suitably be effected by azeotropic distillation of the organic solvent and the water of reaction and subsequent evaporation of the organic solvent.

The objects of this invention are realized by a catalyst comprising phosphorus and vanadium. The catalyst can optionally also contain a co-metal. Typically, the co-metal can be molybdenum, zinc, uranium, magnesium, calcium, scandium, yttrium, lanthanum, cerium, chromium, manganese, iron, nickel, copper, aluminum, gallium, indium, silicon, germanium, tin, bismuth, antimony or tellurium. The total atomic ratio of the co-metal to vanadium advantageously is in the range of 0.001:1 to 0.4:1. It is preferred that the total atomic ratio of the co-metal to vanadium should be in the range of 0.01:1 to 0.2:1.

The co-metal may be added as a compound together with vanadium or separately introduced into the solution. Suitable co-metal compounds comprise their oxides, nitrates, chloride, hydrogen phosphate, sulfate, acetates and other soluble co-metal salts. If it is desired to improve physical properties of the catalyst it may be treated with the suspension of an inert support, for example, alumina, titania, silicon carbide, kieselguhr, pumice or preferably silica. The catalyst may be reinforced with such materials at any stage in its preparation.

According to our process, the average valence of vanadium is in the range of about 4.0 to 4.4. In our catalyst preparation, various anhydrous phosphoric acids may be used including ortho-phosphoric, pyrophosphoric, triphosphoric acid or meta-phosphoric acid. Suitable vanadium compounds include: vanadium oxides such as vanadium pentoxide, vanadium trioxide and the like; vanadium oxyhalides such as vanadyl chloride, vanadyl dichloride, vanadyl trichloride, vanadyl bromide, vanadyl dibromide, vanadyl tribromide and the like; vanadium containing acids such as metavanadic acid, pyrovanadic acid and the like; vanadium salts such as ammonium metavanadate, vanadium sulfate, vanadium phosphate, vanadyl formate, vanadyl oxalate and the like. However, vanadium pentoxide is preferred.

It has been discovered that the catalyst has a characteristic X-ray diffraction pattern as follows:

| d angstrom | Line Position 2.θ degrees | Intensity |
|---|---|---|
| 5.7 | 15.6 | 67 |
| 4.5 | 19.7 | 47 |
| 3.7 | 24.3 | 36 |
| 3.3 | 27.1 | 53 |
| 3.1 | 28.8 | 26 |
| 2.9 | 30.5 | 100 |
| 2.8 | 32.2 | 17 |
| 2.7 | 33.7 | 20 |

In the prior art particularly in U.S. Pat. No. 3,864,280 it is indicated that the selectivity of the oxidation catalyst is directly related to the B phase structure exhibiting a characteristic X-ray diffraction pattern as listed in Table I below:

TABLE 1

| d angstrom | Line Position 2.θ degrees | Intensity, I |
|---|---|---|
| 6.3 | 14.2 | 10 |
| 4.8 | 18.5 | 7 |
| 3.9 | 23.0 | 100 |
| 3.13 | 28.5 | 58 |
| 2.98 | 30.0 | 29 |
| 2.65 | 33.8 | 7 |

Applicant has discovered a new phosphorus-vanadium catalyst having a unique X-ray diffraction pattern. This pattern is retained even if the co-metals named above are added. The catalyst having this pattern exhibits excellent catalytic activity including selectivity and yields in the oxidation of butane to maleic anhydride at a temperature of about 600° to 750° F.

This catalyst shows excellent selectivity and yield in the manufacture of maleic anhydride from butane, thus making it useful for the commercial production of maleic anhydride.

In a preferred embodiment, a solution of a vanadium compound in the hydrocarbon solvent is produced by the reduction of vanadium pentoxide with gaseous hydrogen chloride. The temperature at which the vanadium oxide is reduced is in the range of 32° to 250° F. and preferably 100° to 150° F. After reduction, phosphorus is added suitably as orthophosphoric acid, preferably as 100% orthophosphoric acid. After precipitation of the catalyst and a suitable digestion period, it is filtered from the mother liquor and dried in a vacuum oven at about 200° to 250° F. under a positive nitrogen bleed. The dried catalyst may be activated by heating it in the presence of a hydrocarbon such as n-butane. If a co-metal is used, the co-metal in its oxide form may be added to the solution of the vanadium compound in the hydrocarbon solvent prior to the reduction with the gaseous hydrogen chloride.

This invention also comprises a process for oxidizing butane to maleic anhydride by contacting it in the presence of oxygen with the novel catalyst. The oxidation of butane to maleic anhydride may be accomplished by contacting n-butane in low concentration in oxygen with the described catalyst. Air is entirely satisfactory as a source of oxygen but synthetic manufactures of oxygen and diluent gases such as nitrogen also may be employed. Air enriched with oxygen may be used.

The gaseous feed stream to the oxidation reactors will normally contain air and about 0.2 to about 1.7 mole percent of n-butane. About 0.8 to 1.5 mole percent of n-butane is satisfactory for optimum yield of maleic anhydride for the process of this invention. Although higher concentrations may be employed, explosive hazards may be encountered. Lower concentrations of butane, less than about one percent, of course, will reduce the total yield obtained at equivalent flow rates and, thus, are not normally economically employed. The flow rate of the gaseous stream through the reactor may be varied within rather wide limits, but preferred range of operations is at the rate of about 100 to 4000 cc of feed per cc of catalyst per hour, and more preferably about 1000 to 2400 cc of feed per cc of catalyst per hour. Residence times of the gas stream will normally be less than about four seconds, more preferably less than about one second, and down to a rate where less efficient operations are obtained. The flow rates and residence times are calculated at standard conditions of 760 mm of mercury and at 25° C. A variety of reactors will be found to be useful and multiple tube heat exchanger type reactors are quite satisfactory. The tops of such reactors may vary in diameter from about one-quarter inch to about three inches, and the length may be varied from about three to about ten or more feet. The oxidation reaction is an exothermic reaction and, therefore, relatively close control of the reaction temperatures should be maintained. It is desirable to have the surface of the reactors at a relatively constant temperature and some medium to conduct heat from the reactors is necessary to aid temperature control. Such medium may be Woods metal, molten sulfur, mercury, molten lead and the like, but it has been found that eutectic salt baths are completely satisfactory. One such bath salt is a sodium nitrate, sodium nitrite-potassium nitrate eutectic constant temperature mixture. An additional method of temperature control is to use a metal block reactor whereby the metals surrounding the tube act as a temperature regulating body. As will be recognized by a man skilled in the art, the heat exchanger medium may be kept at the proper temperature by heat exchangers and the like. The reactor or reaction tubes may be iron, stainless steel, carbon steel, nickel, glass tubes such as vycor and the like. Both carbon steel and nickel tubes have excellent long life under the conditions of the reaction described herein. Normally, the reactors contain a preheat zone under an inert material such as one-quarter inch Alundum pellets, inert ceramic balls, nickel balls, or chips and the like present at about one-half to one-tenth the volume of the active catalyst present.

The temperature of the reaction may be varied within some limits, but normally the reaction should be conducted at a temperature within a rather critical range. The oxidation reaction is exothermic and once reaction is underway, the main purpose of the salt bath or other media is to conduct heat away from the reactor and control the reaction. Better operations are normally obtained when the reaction temperature employed is no greater than 20°–50° F. above the salt bath temperature. The temperature of the reactor, of course, will also depend to some extent upon the size of the reactor and the butane concentration.

The reaction may be conducted at atmospheric, super atmospheric, or below atmospheric pressure. The exit pressure will be at least slightly higher than the ambient pressure to insure a positive flow from the reaction. The pressure of the inert gases must be sufficiently higher to overcome the pressure drop through the reactor.

Maleic anhydride may be recovered by a number of ways well known to those skilled in the art. For example, the recovery may be by direct condensation or by absorption in suitable media, with specific operation and purification of the maleic anhydride.

The following examples will serve to provide a fuller understanding of the invention, but it is to be understood that these examples are given for illustrative purposes only and will not be interpreted as limiting the invention in any way. In the examples the terms "conversion", "selectivity" and "yield" are defined as follows:

Conversion % = $\frac{\text{Moles hydrocarbon reacted}}{\text{Moles hydrocarbon in feed}} \times 100$ Selectivity % = $\frac{\text{Moles maleic formed}}{\text{Moles hydrocarbon consumed}} \times 100$ Yield Wt. % = (Conversion) × (Selectivity) × 1.69

EXAMPLE 1

To a 3-neck 2-liter flask equipped with a mechanical stirrer, thermometer, barrett trap, and reflux condenser are added 47.1 g (0.26 m) of $V_2O_5$ and 400 ml of absolute ethanol. The solution is refluxed and 28.9 g of glycerol is added. An additional 26.4 g of glycerol is added at a later time. After reduction is complete, 63.4 g (0.65 m) of 100% crystalline orthophosphoric acid is added; 200 ml of benzene is added and the mixture is allowed to azeotropically distill. After removal of water, the solution is cooled, filtered and washed with methanol. The solids are dried in a vacuum oven under $N_2$ at 250° F.

P/V bulk analysis 0.9/1.0; P/V ratio (top several layers by ESCA) 1.2/1.0; X-ray as shown below, no phase B; surface area by Digisorb 49.1 m²/g; average pore radius based on volume by desportion 219 A.

A sample of this catalyst is analyzed by X-ray and gives the following results:

| angstrom | Line Position 2.θ degrees | Intensity |
| --- | --- | --- |
| 5.7 | 15.6 | 67 |
| 4.5 | 19.7 | 47 |
| 3.7 | 24.3 | 36 |
| 3.3 | 27.1 | 53 |
| 3.1 | 28.8 | 26 |
| 2.9 | 30.5 | 100 |
| 2.8 | 32.2 | 17 |
| 2.7 | 33.7 | 20 |

EXAMPLE 2

The catalyst prepared as in Example 1 is combined with 5% sterotex and formed into ⅛" pills for catalyst evaluation. A 4 g loading of catalyst is placed in an evaluation mini-reactor under 1.05% n-butane in synthetic air mixture at a weight hourly space velocity of 1.4. The catalyst is brought to 680° F. over the next several hours and analysis for maleic anhydride is done by gas liquid partition chromotography. Results are as follows:

| Time on Stream (hrs.) | Conversion (butane) | Selectivity (maleic anhydride) | Yield (maleic anhydride) | Temp. (°F.) |
| --- | --- | --- | --- | --- |
| 260 | 86 | 66 | 92 | 680° |
| 650 | 84 | 60 | 84 | 626° |

EXAMPLE 3

A sample of a catalyst removed from an oxidation run similar to Example 2 showed the following results:

| Time on Stream (hrs.) | Conversion (butane) | Selectivity (maleic anhydride) | Yield (maleic anhydride) | Temp. (°F.) |
| --- | --- | --- | --- | --- |
| — | 86 | 61 | 89 | 679° |

This catalyst, on X-ray analysis, showed no phase B and had X-ray spectra as follows.

| angstrom | Line Position 2.θ degrees | Intensity |
| --- | --- | --- |
| 5.7 | 15.6 | 67 |
| 4.5 | 19.7 | 47 |
| 3.7 | 24.3 | 36 |
| 3.3 | 27.1 | 53 |
| 3.1 | 28.8 | 26 |
| 2.9 | 30.5 | 100 |
| 2.8 | 32.2 | 17 |
| 2.7 | 33.7 | 20 |

We claim:

1. A catalyst for the production of maleic anhydride by the oxidation of butane which comprises a phosphorus-vanadium mixed oxide, the atomic ratio of vanadium to phosphorus being in the range of 0.5:1 to 1.25:1 wherein the catalyst has a characteristic powder X-ray diffraction pattern using copper K alpha radiation as follows:

| angstrom | Line Position 2.θ degrees | Intensity |
| --- | --- | --- |
| 5.7 | 15.6 | 67 |
| 4.5 | 19.7 | 47 |
| 3.7 | 24.3 | 36 |
| 3.3 | 27.1 | 53 |
| 3.1 | 28.8 | 26 |
| 2.9 | 30.5 | 100 |
| 2.8 | 32.2 | 17 |
| 2.7 | 33.7 | 20 |

2. The catalyst of claim 1, wherein there are 0.8:1 to 2:1 atoms of phosphorus present for each atom of vanadium.

3. The catalyst of claim 1 wherein a co-metal is used as a promoter wherein the total atomic ratio of the co-metal to vanadium is in the range of 0.001:1 to 0.4:1.

4. A process for the production of the catalyst of claim 1 which comprises reacting and precipitating the phosphorus-vanadium mixed oxide from the reaction mixture in an organic solvent in the presence of water.

5. The process of claim 4 wherein the organic solvent is isobutanol.

6. The process of claim 4 wherein in addition to the organic solvent, benzene or orthoxylene is employed as a co-solvent.

7. A process for the production of the catalyst of claim 3 which comprises precipitating the phosphorus-vanadium mixed oxide and the co-metal complex from an organic solvent in the presence of water.

* * * * *